United States Patent
Kutsenko

(10) Patent No.: US 7,530,981 B2
(45) Date of Patent: May 12, 2009

(54) BLISKUNOV DEVICE FOR ELONGATING LONG BONES

(75) Inventor: Sergey Nikolaevich Kutsenko, Crimea (UA)

(73) Assignee: Crimean Traumatology and Orthopedics Centre Named After A. I. Bliskunov "Abas", Simferopol (UA)

( * ) Notice: Subject to any disclaimer, the term of this patent is extended or adjusted under 35 U.S.C. 154(b) by 552 days.

(21) Appl. No.: 10/504,362

(22) PCT Filed: Feb. 14, 2003

(86) PCT No.: PCT/UA03/00007

§ 371 (c)(1),
(2), (4) Date: Jan. 11, 2005

(87) PCT Pub. No.: WO03/068089

PCT Pub. Date: Aug. 21, 2003

(65) Prior Publication Data

US 2005/0107787 A1 May 19, 2005

(30) Foreign Application Priority Data

Feb. 18, 2002 (UA) ............................... 2002021344

(51) Int. Cl.
*A61B 17/72* (2006.01)
(52) U.S. Cl. ......................................................... 606/63
(58) Field of Classification Search ................... 606/63, 606/60, 62, 64–68; 29/258–262
See application file for complete search history.

(56) References Cited

U.S. PATENT DOCUMENTS 5,350,379 A * 9/1994 Spievack ...................... 606/63
5,505,733 A * 4/1996 Justin et al. ................... 606/63

* cited by examiner

*Primary Examiner*—Eduardo C Robert
*Assistant Examiner*—Richard Shaffer
(74) *Attorney, Agent, or Firm*—The Nath Law Group; Derek Richmond; Jiaxiao Zhang

(57) ABSTRACT

This invention relates to medicine, in particular to surgical devices for curing the locomotor apparatus with the aid of osteosynthesis. In order to improve operational reliability during implantation, the structure of the inventive device for elongating long bones is embodied in such a way that the axes of the bearing part and the thread screwed part of a screw-holder are offset at a distance ranging from 0.5 to 0.8 mm. A boss (bulge) is embodied on the external body of the device on the side of the orifice in which said screw-holder is fixed. The specific structural embodiment of a finger makes it possible to reduce the traumatic effects of a surgical operation.

2 Claims, 4 Drawing Sheets

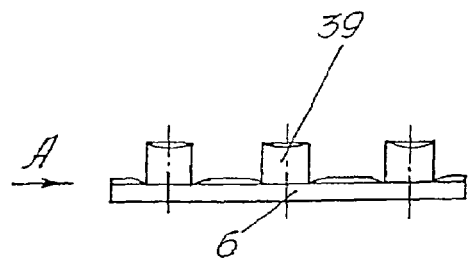
Fig. 6
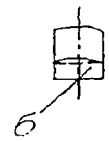
Fig. 7
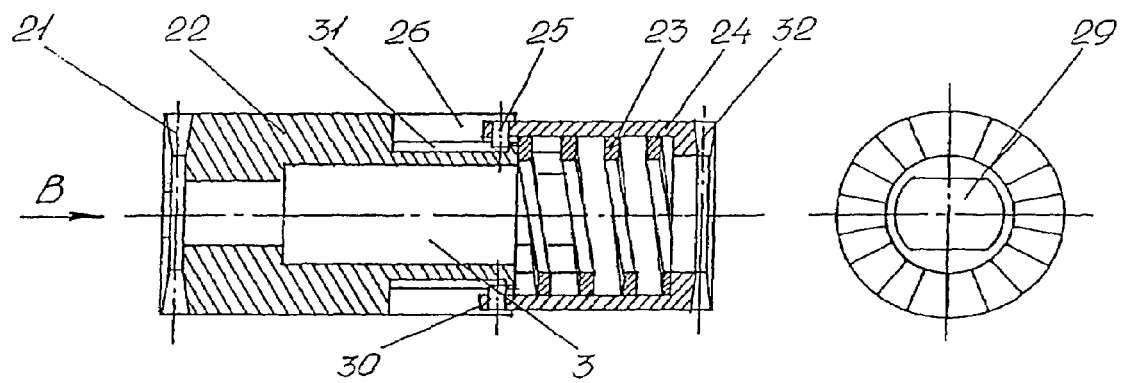
Fig. 8 Fig. 9
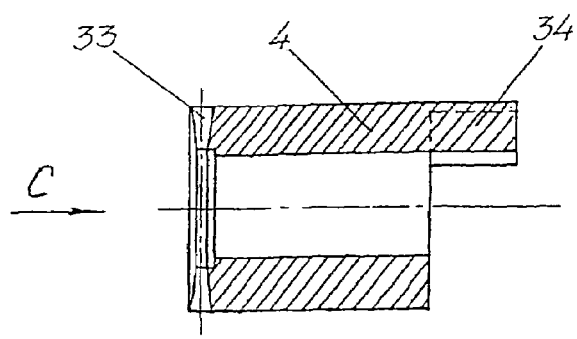
Fig. 10
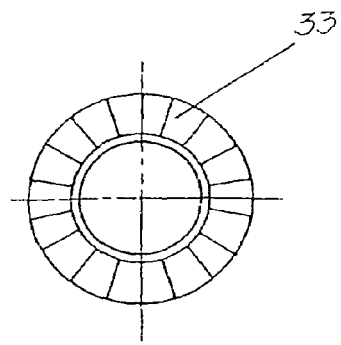
Fig. 11

BLISKUNOV DEVICE FOR ELONGATING LONG BONES

BACKGROUND OF THE INVENTION

This invention relates to medicine, namely to surgical devices for curing the locomotor apparatus using osteosynthesis.

STATE OF THE ART

The known prior art of the invention is the long bone lengthening device (Ukrainian patent 34990A, 15.03.2001). The device contains an external body and an internal pullout hollow cylindrical body connected with each other telescopically and equipped with a boss and a groove. The internal body contains the through orifices for retention screws. The wall of the external body contains a threaded orifice with a screw-holder mounted in it. The screw-holder consists of a bearing part with a transverse through threaded orifice for a check screw and a thread screwed part, both parts coaxial. The device contains a ratchet-and-pawl connected with the external body and including a driving ratchet-wheel with ratchet teeth, which contains a body, a driven teethed ratchet-wheel with a body of its own, a retention ratchet-wheel, a lead screw which is located inside the bodies, connected by means of a screw joint with the internal pullout hollow body and is completed with a shank-end of a figured non-circular section for interaction with a similar figured orifice located in the body of the driven ratchet-wheel, a thrust ring for the lead screw connected monolithically with the external body, a telescopic rodded drive with a sphere, which contains a body and a rod and is capable of moving in the body, one side of which is connected by means of ears through the axis with a finger, on which a nut with a stop, a washer and a lock-nut is screwed, while the other side is connected through a swing joint's sphere with the driving ratchet-wheel of the ratchet-and-pawl, which in its turn is connected with the external body by means of a bayonet joint. The surface of the driving ratchet-wheel body is equipped with grooves, non-through in length and depth, which lead onto the end surface. The driving ratchet-wheel contains a bushing which has, on one side, end surface bosses to fit into the grooves located in the body of the driving ratchet-wheel, elements of anchoring the bushing onto the body of the driving ratchet-wheel, and a spring located in the bushing, on the other side of which there are end surface ratchet teeth. On one side the end surface of the body of the driven ratchet-wheel has ratchet teeth for interaction with the ratchet teeth of the bushing of the driving ratchet-wheel, while on the other side of the surface of the body of the driven ratchet-wheel there are grooves, non-through in length and depth, which lead out onto the end surface. The driven ratchet-wheel also contains a bushing, in which there are end surface bosses to fit into the grooves of the driven ratchet-wheel body, elements of anchoring the bushing of the driven ratchet-wheel onto the driven ratchet-wheel body, and a spring located also in this bushing, on the other side of which there are also end surface ratchet teeth, whose direction is opposite to that of the ratchet teeth of the driving ratchet-wheel's bushing. The retention ratchet-wheel has the shape of a stop sleeve, which on one end surface has ratchet teeth for interaction with the driven ratchet-wheel's bushing, while on the other end surface it has bosses to fit into the groove in the monolithic thrust ring of the external body. The boss of the external body is made in the shape of a hemiprismatic dowel, three lateral sides of which have flat surfaces, while on the external surface of the fourth lateral side, which fits into the inner surface of the external body, there are cylinder-shaped bosses monolithic with the dowel and designed in such a way that they can be inserted into the through orifices in the external body. The height of the dowel's bosses corresponds to the thickness of the external body wall. In the grooves of the ratchet-wheels' bodies there are additional closed contour hollows. The elements of anchoring the bushings of the ratchet-wheels onto the bodies of the ratchet-wheels are joint pins mounted in the orifices of the bosses. They are inserted into the additional hollows of the grooves, with a possibility for the bushings to move freely with respect to the bodies.

The closest prior art features similar to those of the device for elongating long bones by the present invention are as follows: the external body and the internal pullout cylindrical bodies, connected telescopically with each other, both bodies having the boss and the groove, the through orifices in the internal bodies for the retention screws, the threaded orifice in the wall of the external body with a screw-holder mounted in it, the screw-holder containing the bearing part and the thread screwed part, the ratchet-and-pawl connected with the external body and including the driving teethed ratchet-wheel which contains a body, the driven teethed ratchet-wheel which contains a body, the retention ratchet-wheel, the lead screw located inside the bodies, connected by means of a screw joint with the internal pullout hollow body and equipped with the shank end of figured non-circular section for interaction with the similar figured orifice made in the driven ratchet-wheel's body, the thrust ring for the lead screw, monolithical with the external body, the telescopic rodded drive with the sphere, which contains a body, and the rod made so that it can move inside the body, which is connected on one side by means of ears through the axis with the finger, while on the other side it is connected through the sphere of the swing joint with the driving ratchet-wheel of the ratchet-and-pawl, which in its turn is connected with the external body by means of the bayonet joint, with the grooves, non-through in length and depth, made in the body of the driving ratchet-wheel and leading out onto the end surface. The driving ratchet-wheel contains the bushing, which has on the end surface the bosses to fit into the grooves in the body of the driving ratchet-wheel, and the spring located in the bushing, on the other side of which there are the end surface ratchet teeth for interaction with the ratchet teeth of the driving ratchet-wheel. On the surface of the other side of the driven ratchet-wheel there are the grooves, non-through in length and depth, which lead out onto the end surface. The driven ratchet-wheel also contains the bushing, in which there are the end surface bosses to fit into the grooves of the driven ratchet-wheel. Then there are the elements of anchoring the bushing of the driven ratchet-wheel onto the body of the driven ratchet-wheel, and the spring located also in this bushing, on the other side of which there are also the end surface ratchet teeth, the direction of which being opposite to that of the ratchet teeth of the driving ratchet-wheel's bushing. The retention ratchet-wheel has a shape of a stop sleeve, one end surface of which is equipped with the ratchet teeth for interaction with the bushing of the driven ratchet-wheel and the other end surface has a boss to fit into the groove made in the stop collar for the lead screw, which in its turn is made monolithically with the external body. The boss of the external body has the shape of a hemiprismatic dowel, three lateral sides of which have flat surfaces, while on the outer surface of the fourth lateral side, which fits into the inner surface of the external body, there are the cylindrical bosses made monolithically with the dowel and so that they can be inserted into the through orifices on the external body. The height of the bosses of the dowel corresponds to the thickness of the external body's wall. The grooves of the ratchet-wheels' bodies contain the additional closed contour hollows, while the bosses of the bushings of the ratchet-wheels have the orifices. The elements of anchoring the ratchet-wheels' bushings onto the ratchet-wheels' bodies are the joint pins, which are mounted in the orifices of the bosses and inserted into the additional hollows of the grooves. The bushings can move freely with respect to the bodies.

However, the above-mentioned device has the following shortcomings.

The mounting of the check screw into the transverse threaded orifice of the bearing part is necessary in order to prevent self-unscrewing of the screw-holder under the influence of varying dynamic load which emerges when lengthening the limb. To mount the check screw it is necessary to make channels on the front and rear surfaces of the trochanterian region of the bone. The check screw can only be mounted with the help of a special conductor as the tool used for making a transverse orifice in the bone penetrates at an angle to the curved surface, which may cause tool deviation. All these actions require extra time during surgical treatment.

Therefore, three orifices located in the same plane are made on a limited area of the bone, which definitely weakens the bone in the said section.

A small thickness of the wall of the external body in the place where the threaded orifice is made, into which the screw-holder is to be mounted, does not provide a sufficient strength of the screw joint of the screw-holder and the external body.

During surgical treatment, the finger (having the structure by the prior art, i.e. a screwed-on nut equipped with a stop member, washer and a lock-nut) is inserted into the through orifice in the iliac bone, which is preceded by exfoliation of the soft tissues off the outer surface of the bone. To fix the finger the nut should be screwed up onto the inner surface of the iliac bone, which is preceded by exfoliation of the soft tissues off the inner surface of the bone. Such exfoliation is traumatic. Besides, there exists a danger of injuring the peritoneum.

SUMMARY OF THE INVENTION

The problem of the present invention is to improve the device for elongating long bones wherein the constructive particularities provide for the improved reliability of functioning of the implanted device when power load is increased, as well as reducing the time of surgical treatment and decreasing the trauma rate when implanting the device.

This technical problem is solved as follows. The device for elongating long bones consists of the external body and the internal cylindrical pullout hollow bodies connected telescopically, which are equipped with a boss and a groove. The internal body has through orifices to fit into the retention screws, while in the wall of the external body there is a threaded orifice with a screw-holder mounted into it. The screw-holder contains the bearing part and the thread screwed part. The ratchet-and-pawl is connected with the external body and includes the driving ratchet-wheel with the ratchet teeth, which contains a body, then there is a driven teethed ratchet-wheel, which contains a body, a retention ratchet-wheel, a lead screw located inside the bodies and connected with the help of a screw joint with the internal pullout hollow body. It is also equipped with the shank end of figured non-circular section for interaction with a similar figured orifice made in the body of the driven ratchet-wheel. Next, there is a thrust ring for the lead screw made monolithically with the external body, a telescopic rodded drive with a sphere, which contains a body and a rod and which can move freely inside the body. On one side it is connected with the help of the ears through the axis with the finger, while on the other side it is connected through the sphere of the swing joint with the driving ratchet-wheel of the ratchet-and-pawl, which in its turn is connected with the external body by means of a bayonet joint. On the surface of the body of the driving ratchet-wheel there are grooves, non-through in length and depth, which lead out onto the end surface. The driving ratchet-wheel contains a bushing, on one side of which there are bosses to fit into the grooves made in the body of the driving ratchet-wheel, it further contains the elements of anchoring the bushing onto the body of the driving ratchet-wheel, and a spring located in the bushing, on the other side of which there are end surface ratchet teeth. On one side of the end surface of the body of the driven ratchet-wheel there are ratchet teeth for interaction with the ratchet teeth of the driving ratchet-wheel's bushing, while on the other side of the surface of the driven ratchet-wheel's body there are grooves, non-through in length and depth, which lead out onto the end surface. The driven ratchet-wheel also contains a bushing, on one side of which there are end surface bosses to fit into the grooves of the body of the driven ratchet-wheel. Further there are the elements of anchoring the driven ratchet-wheel's bushing onto the driven ratchet-wheel's body, and a spring, which is also located in this bushing, on the other side of which there are also end surface ratchet-teeth. The direction of these ratchet teeth is opposite to that of the ratchet teeth of the driving ratchet-wheel's bushing. The retention ratchet-wheel has a shape of a stop sleeve, which is equipped on one end surface with the ratchet teeth for interaction with the bushing of the driven ratchet-wheel, while on the other end surface it has bosses to fit into the groove made in the thrust ring for the lead screw, which is made monolithically with the external body. The boss of the external body has a shape of a hemiprismatic dowel, three lateral sides of which have flat surfaces, while on the outer surface of the fourth lateral side, which fits into the inner surface of the external body, are located cylindrical bosses made monolithically with the dowel, which can be inserted into the through orifices on the external body. The height of the bosses of the dowel corresponds to the thickness of the wall of the external body. In the grooves of the bodies of the ratchet-wheels there are some additional closed contour hollows. And there are orifices in the bosses of the bushings of the ratchet-wheels. The elements of anchoring the ratchet wheels' bushings to the ratchet-wheels' cases are joint pins mounted into the bosses' orifices, which are inserted into the additional hollows of the grooves with a possibility for the bushings to move freely with respect to the bodies. By the invention, the axis of the threaded part is shifted with respect to the axis of the bearing part of the screw-holder by 0.5-0.8 mm. On the external body, in the proximity to the threaded orifice, into which the screw-holder is mounted, there is a boss, while in the finger, which is connected through the axis with the coupling rod, there is a clamp and an end surface orifice, both located on the side of the rod. A plate for the ears with a orifice for the axis is screwed into the orifice and another through threaded transverse orifice is made to fit into the lock screw of the crest of the iliac bone.

There exists the following cause-effect connection between the totality of the essential features of the invention and the achieved technical result:

The 0.5-0.8 mm shift of the axes of the bearing part and the thread screwed part of the screw-holder will provide a due self-locking of the latter, which will permit to avoid unscrewing. If the shift is less than 0.5 mm, it will not secure against unscrewing. If the shift is more than 0.8 mm, it may cause difficulty in mounting and dismounting of the screw-holder in the bone due to scarcity of space.

Making a boss (bulge) on the external body in the proximity to the threaded orifice, into which the screw-holder is mounted, will provide sufficient thickness of the body wall where the threaded orifice is located. The medullary cavity in the upper, proximal part of the limb bone where the external body will be located has a physiological dilatation, which makes the boss admissible.

Using the structure of the finger connected through the axis with the rod, made as an assembly, with a clamp and an end surface orifice, into which the plate for the ears with a orifice for the axis is screwed, and with a through threaded transverse orifice for the blocking screw of the crest of the iliac bone, will permit to lower the trauma rate of surgical treatment. The crest of the iliac bone is easily found in the course of palpation. In order to mount the blocking screw, it is merely required to make a cut in the skin and drill a orifice in the crest.

The above-listed features improve the reliability of the functioning of the implanted device.

BRIEF DESCRIPTION OF THE FIGURES

The invention is illustrated with the graphic matter wherein.

THE DETAILED DESCRIPTION OF THE EMBODIMENT

Figure 1:
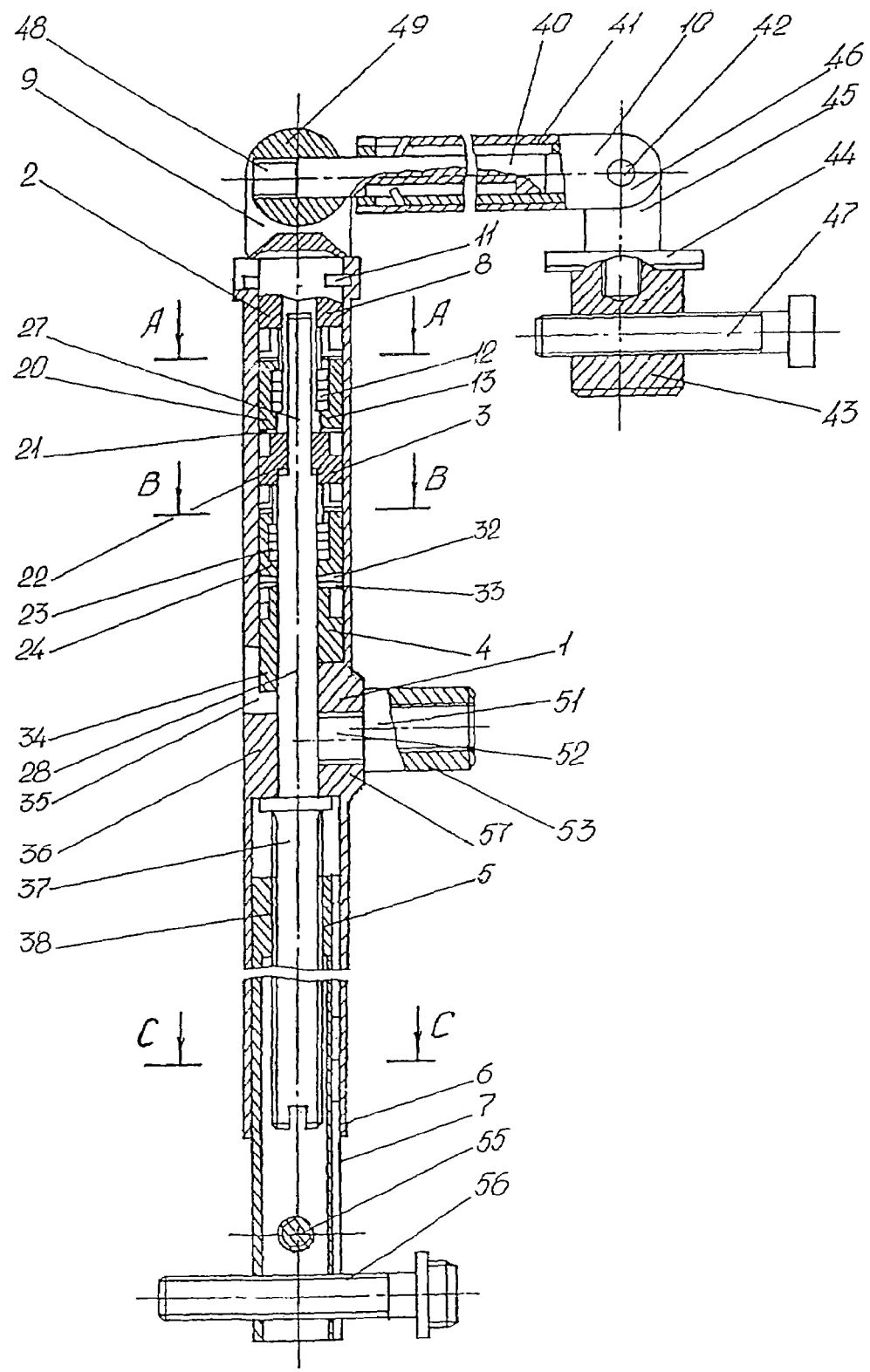
FIG. 1—overall view of the device in section
FIG. 2—section A-A of FIG. 1
FIG. 3—section B-B of FIG. 1
FIG. 4—section C-C of FIG. 1
FIG. 5—fragment of driving ratchet-wheel
FIG. 6—hemiprismatic dowel
FIG. 7—view A of FIG. 6
FIG. 8—driven ratchet-wheel
FIG. 9—view B of FIG. 8
FIG. 10—retainer ratchet-wheel (stop sleeve)
FIG. 11—view C of FIG. 10
FIG. 12—device implantation diagram
Figure 2:
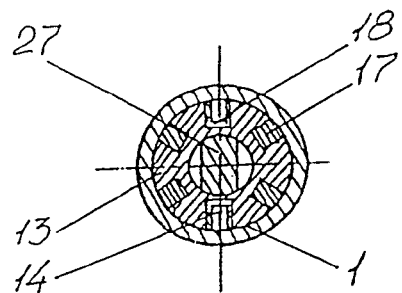
Figure 5:
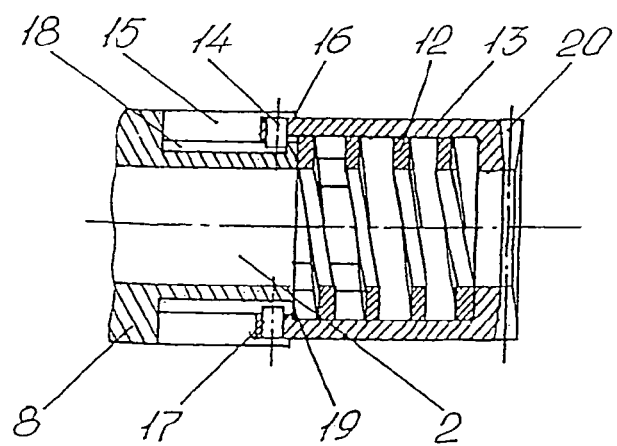
Figure 12:
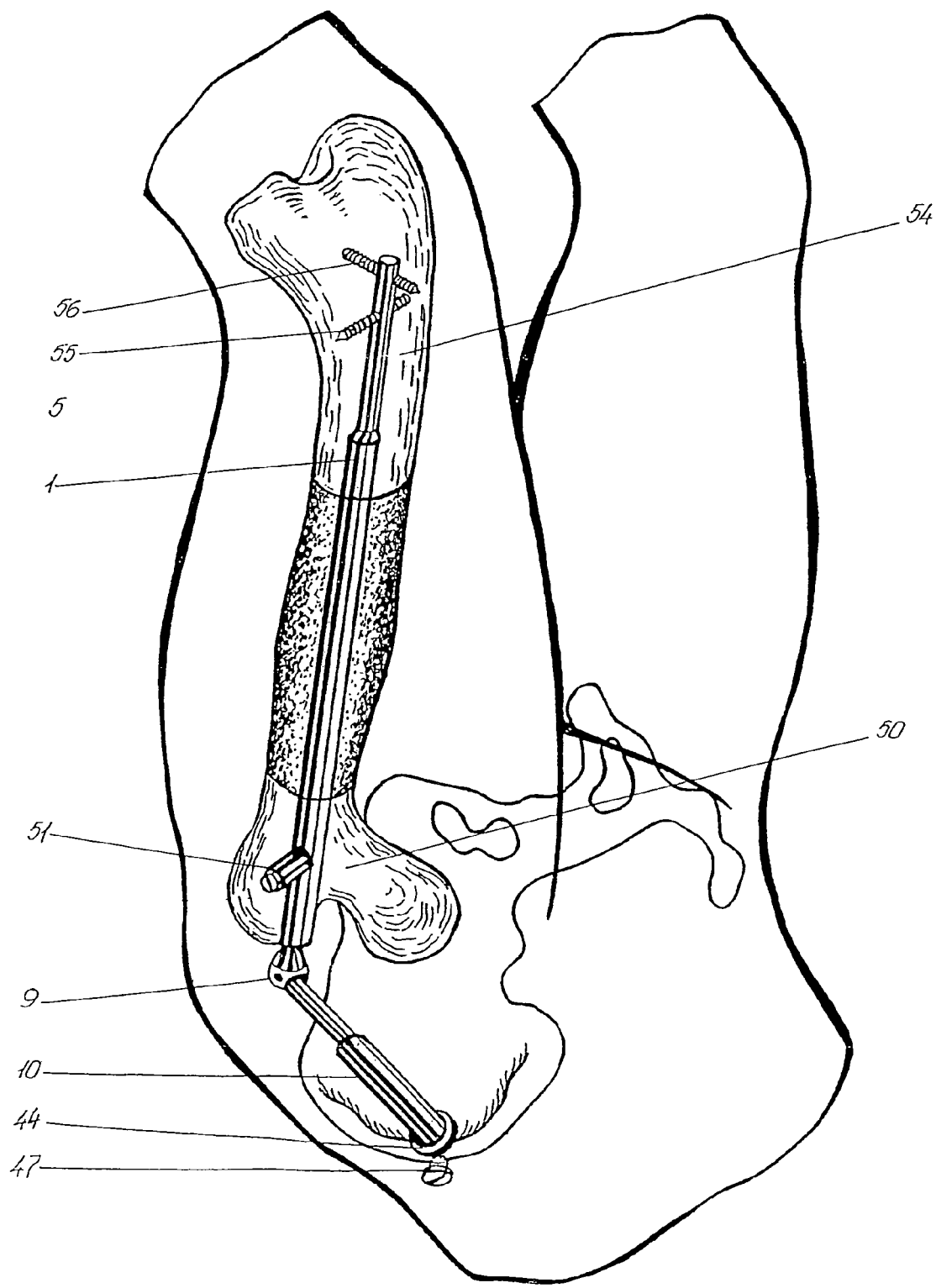

The device consists of external body 1 with ratchet-and-pawl mounted in it. The latter contains driving ratchet-wheel 2 in assembly, driven ratchet-wheel 3 in assembly, retainer ratchet-wheel 4 and pullout internal body 5. Sliding boss-groove joint between telescopic external body 1 and internal pullout body 5 is made so that hemiprismatic dowel (boss) 6 located on the inner wall of external body 1 interacts with groove 7 of internal body 5. Driving ratchet-wheel 2 contains body 8 connected on one side by means of swing joint 9 with telescopic rodded drive 10 and bayonet joint 11—with external body 1, while on the other side (see FIG. 5)—with spring 12, bushing 13 and two joint pins 14. Body 8 has six grooves 15, non-through in length and depth, which are inserted into end surface 16 with six bosses 17 of bushing 13 inserted into them with clearance fit (see FIG. 2). Besides, in two opposite grooves 15 of body 8 there are additional closed contour hollows 18, into which joint pins 14 are inserted, so that bushing 13 can freely move with respect to body 8 and which can be kept in assembly due to pads (shoulders) 19 of body 8. On the side opposite to bosses 17 bushing 13 has ratchet teeth 20 for interaction with teeth 21 of driven ratchet-wheel 3 (see FIG. 8). Driven ratchet-wheel 3 contains body 22, spring 23 and bushing 24 with two joint pins 25. On one side, body 22 has ratchet teeth 21 and on the other side six grooves 26, whose design is similar to that of grooves 15 in body 8 of driving ratchet-wheel 2. Body 22 of driven ratchet-wheel 3 is connected with shank end 27 of lead screw 28, which is also located inside bodies 1, 5 and 8 and bushings 4, 13 and 24 in noncircular figured orifice 29. The structural design of bushing 24 with two joint pins 25 is similar to the design of bushing 13. It also has six bosses 30 inserted into grooves 26, while in two opposite grooves 26 are also made additional hollows 31, where joint pins 25 are inserted. On the opposite side, bushing 24 has ratchet teeth 32, which interact with teeth 33 of retainer ratchet-wheel 4 and have mutually opposite directions (see FIGS. 8, 9, 10, and 11). Retainer ratchet-wheel 4 is made in the shape of a bushing which on one side has ratchet teeth 33, while on the other side there is boss 34 made so that it can be inserted into groove 35 made in monolithic thrust ring 36 of external body 1. Threaded part 37 of lead screw 28 has a screw joint with threaded area 38 of internal body 5, whose length corresponds to the estimated lengthening of the bone. FIG. 6 shows the hemiprismatic dowel 6, whose structure has got an essential advantage due to the increase in number of its bosses 39, which permits to strengthen the mechanical characteristics of dowel 6 without deteriorating the resistance of the wall of body 1 to power load. Mounting dowel 6 on the inside wall of body 1 will make it possible to encase it in closed space between the wall of external body 1 and groove 7 of pullout internal body 5, which helps to resolve the problem of its safe anchoring. Rod 40 of rodded drive 10, which is made so that it can shift in body 41, is connected with finger 43 through axis 42. Finger 43 is equipped with clamp 44 and end surface orifice with plate 45 for ears 46 screwed into it. In finger 43 there is a through threaded transverse orifice for blocking screw 47 of the crest of the iliac bone. Rod 40 is connected by means of screw joint 48 with sphere 49 of swing joint 9. Body 1 is fixed onto proximal bone fragment 50 (see FIG. 12) using screw-holder 51 equipped with threaded part 52 and bearing part 53. A 0.5-0.8 mm shift of axes of threaded part 52 and bearing part 53 of screw-holder 51 provides self-locking which prevents screw-holder 51 against unscrewing. Body 5 is fixed onto distal bone fragment 54 with retention screws 55 and 56 inserted into the orifice of body 5. On the side of the threaded orifice on external body 1, into which screw-holder 51 is mounted, there is boss (bulge) 57 to provide sufficient thickness of the wall of body 1.

Figure 3:
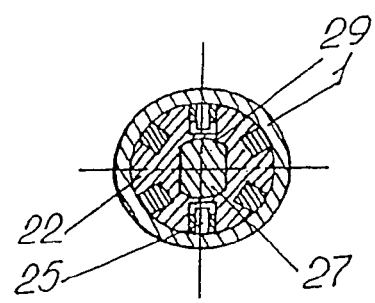
Figure 4:
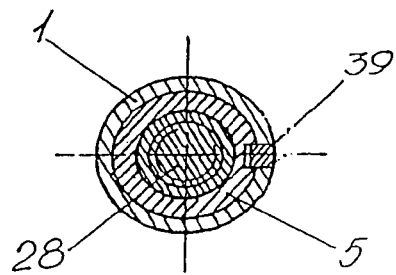

The ratchet-and-pawl of the device works as follows:

When driving ratchet-wheel 2 is turned counterclockwise (as seen from where telescopic rodded drive 10 is) by the angular distance of the ratchet-and-pawl, due to the linkage of teeth 20 and 21, driven ratchet-wheel 3 will be turning simultaneously, transmitting rotation to lead screw 28 through noncircular profiled joint 29 (see FIG. 3). At this point, bushing 24 acts as a locking device and its teeth 32 jump over teeth 33 of stop sleeve 4.

When driving ratchet-wheel 2 is turned clockwise, an idle stroke is performed, with teeth 20 of bushing 13, which at this point acts as a ratchet, jumping over teeth 21 of body 22 of driven ratchet-wheel 3. At this point stop sleeve 4, whose teeth 33 will be interacting with teeth 32 of bushing 24, will not let driven ratchet-wheel 3 make a turn. At such a pattern of interaction of the components of the ratchet-and-pawl, the power load acting on the device will not in any way affect the reliability of its functioning.

The advantage of the structure of dowel 6 (see FIGS. 6 and 7) lies in the fact that due to the increase in the number of bosses 39 it is possible to calculate its requisite mechanical characteristics without weakening the resistance of the wall of body 1 to power load. Mounting dowel 6 on the inside wall of body 1 makes it possible to locate it in closed space between the wall of external body 1 and groove 7 of internal body 5, which helps to resolve the problem of its reliable anchoring.

During surgical treatment the patient is laid on his/her side so that the limb to be operated on should be bent in the knee and hip joints. Cuts in the soft tissues are made over the greater trochanter and over the upper flaring portion of the iliac bone. Using a drill, whose diameter corresponds to the outer diameter of body 1, a channel in the medullary cavity of the femur is drilled through the greater trochanter to the depth required for mounting of the entire device. Next comes osteotomy (bone cutting), which is done by any known way, which helps get two bone fragments: proximal 50 and distal 54. Fragment 54 is fixed onto internal body 5 using screws 55 and 56, while in fragment 50 mutually two perpendicular orifices for screws 51 and 52 are drilled. The device is placed inside the femur, screw 51 is screwed into body 1 through the cortical layer of the femur. Next, the telescopic rodded drive is introduced through the greater and medium sciatic muscles, a transverse orifice is drilled in the wing of the iliac bone, and finger 43, equipped with clamp 44 and end surface orifice with plate 45 for ears 46 screwed into it, is inserted into this transverse orifice. Through axis 42 finger 43 is connected with body 42. A cut is done on the skin over the crest of the iliac bone, and a orifice coaxial with the transverse orifice in finger 43, through which it is fixed by means of blocking screw 47, is drilled in the bone. The wounds are then sutured. During the postoperative period, after removal of stitches the patient is asked to turn his/her leg around the long axis of the hip first inwards then outwards. The number of teeth in ratchet-wheels 2 and 3 and in bushing 4 is 18 each, while the actuation (functioning) angle makes up 20°.

When turning the hip inwards (working stroke) telescopic rodded drive 10 returns driving ratchet-wheel 2 through swing joint 9 back to the actuation angle and through teeth 20 of its bushing 13 transmits the torque on tooth 21 to body 22 of driven ratchet-wheel 3. Driven ratchet-wheel 3 further transmits the torque onto lead screw 28 through the joint of noncircular figured shank end 27 and orifice 29. At this point, teeth 32 of bushing 24 of driven ratchet-wheel 3, acting as a spring loaded ratchet, jump over the teeth of retainer ratchet-wheel 4.

When turning the hip outwards (idle stroke) the formed power circuit (lead screw 28, pullout body 5, retainer wheel 4, driven ratchet-wheel 3) fixes body 22 of driven ratchet-wheel 3 against the axis shift with respect to shank end 27 of lead screw 28, while teeth 20 of bushing 13 of driving ratchet-wheel 2 jump over teeth 21 of body 22 of driven ratchet-wheel 3, which makes bushing 13 interlock for the next working stroke. At a such kinematic pattern of the ratchet-and-pawl, the body of driven ratchet-wheel 22 is kept permanently fixed against the axial shift by forces of friction, both during the working and idle strokes of the ratchet-and-pawl. The functions of shifting are performed by bushings 13 and 24 mounted outside the zone of action of the power circuit.

The number of couples of turns within 24 hours is chosen depending on the lengthening rate and the step angle of threaded part 37 of lead screw 28. At a 1 mm per 24 hrs lengthening rate and a 1 mm step angle of the threading 18 couples of turns are required within 24 hours. After achievement of the estimated lengthening, e.g. 10 cm, which corresponds to the length of threaded area 38 of body 5, telescopic rodded drive 10 can be removed. For this purpose, a 2-3 cm cut is done in the region of the wing of the iliac bone, connections of finger 43 of telescopic rodded drive 10 with blocking screw 47 and plate 45 are disconnected and rod 40 with sphere 49 is unscrewed. After maturing of the distraction regenerate (i.e. when the density of the callus formed as a result of the bone lengthening equals the density of the bone) the device is to be removed out of the bone as an ordinary intraosseous retainer, for which purpose retention screws 51, 52, 55 and 56 are removed and a cut in the region of the greater trochanter is done.

The invention claimed is:

1. A device for elongating long bones comprising
an external and a pullout internal cylindrical hollow body, connected telescopically, each having a boss and a groove,
said internal body having through orifices for retention screws, a wall of said external body having a threaded orifice with a screw-holder mounted therein, said screw-holder containing a coaxial bearing part and a thread screwed part,
a ratchet-and-pawl gear connected with said external body, a lead screw disposed inside said external body, which is connected by way of a screw joint with the internal pullout hollow body, said ratchet-and-pawl gear being further connected with said lead screw, and having a thrust ring for said lead screw operable to pull out said internal body relative to said external body,
a telescopic rodded drive, with a sphere, said rod drive operable to transmit rotational movement, connected to a driving ratchet wheel by means of a swing joint and to the external body by means of a bayonet joint, said driving ratchet wheel connected to said lead screw,
a key in communication with said external body and said internal body for preventing rotational shifting of the external body relative to said internal body, wherein an axis of said thread screwed part of the screw-holder is shifted relative to an axis of said bearing part by 0.5-0.8 mm,
the external body in said threaded orifice area, where said screw-holder is mounted, having a boss for strengthening said external body, and
a finger connected through an axis of said rod, having, from a side of said rod, a clamp and an end surface orifice, in which a plate for ears with an orifice for the axis is mounted, and a through threaded transverse orifice for a blocking screw of the crest of the iliac bone.

2. A device for elongating long bones comprising
an external and a pullout internal cylindrical hollow body, connected telescopically, each having a boss and a groove,
said internal body having through orifices for retention screws, a wall of said external body having a threaded orifice with a screw-holder mounted therein, said screw-holder containing a coaxial bearing part and a thread screwed part,
a ratchet-and-pawl gear connected with said external body, a lead screw disposed inside said external body, which is connected by way of a screw joint with the internal pullout hollow body, said ratchet-and-pawl gear being further connected with said lead screw, and having a thrust ring for said lead screw operable to pull out said internal body relative to said external body, a telescopic rodded drive, with a sphere, said rod drive operable to transmit rotational movement, connected to a driving ratchet wheel by means of a swing joint and to the external body by means of a bayonet joint, said driving ratchet wheel connected to said lead screw, a key in communication with said external body and said internal body for preventing rotational shifting of the external body relative to said internal body, wherein an axis of said thread screwed part of the screw-holder is shifted relative to an axis of said bearing part by 0.5-0.8 mm, the external body in said threaded orifice area, where said screw-holder is mounted, having a boss for strengthening said external body, and a finger connected proximally through an axis perpendicular to the longitudinal axis of said rod, said finger having, a clamp and an end surface orifice with plate distally connecting said finger to an ear of said rod drive, and said finger having distally a through threaded transverse orifice for a blocking screw of the crest of the iliac bone.

* * * * *